United States Patent [19]

Renzel

[11] 4,098,131
[45] Jul. 4, 1978

[54] METHOD AND APPARATUS FOR INCREASING THE SPEED OF ULTRASONIC PULSE-ECHO TESTING

[75] Inventor: Peter Renzel, Düren, Fed. Rep. of Germany

[73] Assignee: Krautkramer-Branson, Incorporated, Stratford, Conn.

[21] Appl. No.: 763,865

[22] Filed: Jan. 31, 1977

[30] Foreign Application Priority Data

Oct. 15, 1976 [DE] Fed. Rep. of Germany ....... 2646541

[51] Int. Cl.² ............................................. G01N 29/04
[52] U.S. Cl. ......................................... 73/627; 73/609; 73/615; 73/632
[58] Field of Search ............... 73/67.7, 67.8 R, 67.8 S, 73/67.9, 609, 615, 627, 632

[56] References Cited

U.S. PATENT DOCUMENTS 3,929,006  12/1975  Boggs et al. ........................ 73/67.8 S Primary Examiner—Richard C. Queisser
Assistant Examiner—John P. Beauchamp
Attorney, Agent, or Firm—Ervin B. Steinberg; Philip J. Feig

[57] ABSTRACT

In order to increase the speed at which a workpiece is tested by the ultrasonic pulse-echo method, the dead time between individual measurement time intervals is shortened by providing a minimum predetermined time interval selected for the specific test conditions. When an echo responsive signal is manifest in the receiving circuit, in order to prevent the occurrence of phantom echo signals arising in the following measuring interval, the generation of the succeeding transmit signal is inhibited for the predetermined time interval after receipt of the last echo responsive electrical signal of the measuring interval having an amplitude exceeding a predetermined minimum amplitude. The test speed therefore, is made adaptive to the condition of the receipt of the number of echo responsive electrical signals exceeding a predetermined minimum amplitude.

1 Claim, 3 Drawing Figures

METHOD AND APPARATUS FOR INCREASING THE SPEED OF ULTRASONIC PULSE-ECHO TESTING

SUMMARY OF THE INVENTION

This invention broadly refers to pulse-echo ultrasonic testing and more particularly to a method and apparatus for controlling the generation of an ultrasonic transmit pulse signal whose resulting acoustic search signal traverses a workpiece, the transit time of such search signal being used, typically for measuring the thickness of the workpiece.

More specifically, this invention concerns a method and apparatus for increasing the speed of ultrasonic testing by reducing the dead time in an ultrasonic measuring cycle. To this end, the present invention discloses a novel arrangement for producing an ultrasonic transmit signal only when there is an absence of interfering signals in the receiving portion of the test circuit. The interfering signals of concern are those caused by echo signals produced during preceding signal sequences and are known as phantom echoes. As used, the term "phantom echoes" designates echo signals caused by a preceding transmit pulse signal causing an echo sequence, which have not died down in the new single measuring time interval, that is, the echo signals still exceed a predetermined threshold value. A time shortened measuring cycle for determining the thickness of workpieces by ultrasonic energy is most desirable since forming the average value from a plurality of single measuring time intervals may lead to prolonged measuring periods, thereby causing a serious slow down of the speed at which a workpiece can be measured or tested.

The problem of reducing the measuring time occurs not only when measuring workpieces for thickness utilizing ultrasonic energy, but also when searching for defects, that is, when searching for internally disposed material discontinuities. The problem is caused by the fact that interfering echo sequences can arise as the result of signal reflections which are manifest irrespective whether manual or automatic testing is used. The problem also is present when distances are measured with acoustic pulse signals or with pulse signals generated by electromagnetic waves. In manual or automatic testing of workpieces by ultrasonic energy, phantom echoes present during a new or a restarted single measuring time interval interfere with such a measuring interval and necessitate that the already low pulse repetition frequency rate be lowered still further.

It is known to measure the thickness of workpieces or the location of defects by means of the time dependent distance between the transmit pulse and the first echo signal (rear wall echo, or defect responsive echo). This method is known as the transit time measurement of a pulse signal wherein the generation of the transmit pulse signal is used as the zero point of the measuring cycle. The thickness of the workpiece or the depth of the defect then is a function of the transit time of the pulse signal multiplied by the velocity of the acoustic wave in the workpiece. The transit time and, hence, the thickness or length of the workpiece or depth of a defect below the workpiece surface can be indicated on a scale bearing screen of a cathode ray tube, or be indicated in numerals by the use of analog or digital techniques. Determining the position of a defect below the workpiece surface is completely identical with measuring the thickness of a workpiece and both methods will not be described separately in the following text.

When measuring the thickness of workpieces with ultrasonic pulse signals the defect limits are not arbitrarily small. Using digital techniques for measuring a single transit time (single shot technique), time errors occur of a magnitude corresponding to the reciprocal of the counting frequency (bit error). In order to reduce such error it is known to provide a plurality of measurements and form an average value. The error then is reduced by a factor of $1/\sqrt{n}$, wherein n is the quantity of single measurements. It is necessary to perform n such measurement in order to derive a proper measurement value. However, in this latter method the total measuring cycle time is adversely affected, being lengthened by the factor n. As used in this connection, the total measuring cycle time comprises the time duration formed by the sum of all of the single measurement time intervals needed for deriving an average value and the dead time between all of those single measurement intervals. The dead time periods essentially are stand-by periods necessary to permit multiple echoes during the single measurement time interval to decay because otherwise such multiple echoes, known as phantom echoes, interfere with the succeeding single measurement interval and cause wrong measuring results; see "Ultrasonic Testing of Materials" by J. & H. Krautkramer (book), Springer Verlag, New York (1969) 2nd edition; pages 156–157; or 3rd edition (in German language) (1975), pages 196–198.

The length of a single dead time period is dependent largely upon the sensitivity of the test probe, intensity of excitation of the probe, material dependent attenuation of pulse signal amplitude, and upon the workpiece thickness to be measured. A subsequent transmit pulse signal may be generated safely only when no interfering echo signal from a preceding single measuring interval is present. This means, the dead time is a predetermined constant value which must be fixed for th most unfavorable condition and which must be multiplied by the quantity of single measurement intervals forming such a measuring cycle.

The following example more clearly illustrates the time intervals occurring by such measurements.

The thickness of an aluminum plate with a thickness up to $d_{max} = 100$ mm is to be measured. In the present example $V_{L\,min}$ designates the lowest acoustic velocity, which value is dependent upon the workpiece material, and $V_{L\,max}$ designates the maximum acoustic velocity, also material dependent. $V_{L\,Al}$ is the acoustic velocity for longitudinal waves in aluminum, n designates the quantity of individual measuring time intervals necessary for deriving an average value (a constant factor dependent upon acoustic velocity and test system), and $t_{SE}$ is the time dependent interval between two successive transmit pulses, simultaneously this is also the time interval between successive single measurements. Hence, $$t_{SE} \cong \frac{2d_{max}}{V_{Lmin}} \times Z_{max}$$

Designation $t_{ZA}$ is the time duration for a plurality of individual measurements which are necessary to derive the average value. Therefore, $$t_{ZA} = nt_{SE}$$

Factor $Z_{max}$ designates the predetermined maximum quantity of possible rear wall responsive echo signals, under the assumption of good coupling contact between the probe and the workpiece surface and minimum signal attenuation under conditions of optimum test probe characteristics.

Thus, given:

$V_{Lmin}$ to $V_{Lmax} = 1,000$ m/sec to 10,000 m/sec;

In the above example $V_{LAl} = 6,300$ m/sec;
$n = 630$ which is 10% of the acoustic velocity for the present example;
$Z_{max} = 20$;
The transmit pulse signal interval necessary becomes:

$$t_{SE} \geq \frac{2d_{max}}{V_{Lmin}} \times Z_{max} = \frac{0.2m}{1000 \text{ m/sec}} \times 20 = 4 \times 10^{-3} \text{ sec};$$

Hence:

$$t_{SE} \geq 4 \text{ milliseconds}.$$

From the above it follows that the total measuring cycle for an aluminum plate as noted above becomes:

$$t_{ZA} = nt_{SE} \geq 630 \times 4 \times 10^{-3} \text{ sec};$$

$$t_{ZA} \approx 2.5 \text{ sec}.$$

Hence, the measuring cycle frequency becomes $f_{ZA} = 1/t_{ZA}$ which in the present example for aluminum amounts to a readout change occurring every 2.5 seconds, a rather long and unsatisfactory value.

The present invention has for its object a reduction of the measuring cycle when using the average value measuring method while inhibiting concomitantly the interfering effect of phantom echo signals.

The object of this invention is achieved in that the longest transmit pulse sequence time interval selected for the particular measuring process is determined by taking maximum workpiece wall thickness, or length, and minimum acoustic velocity. Frequency determining circuit components are associocated with a monostable multivibrator and this multivibrator always is reset (re-triggered) responsive to interfering signals caused by a preceding transmitted search signal, which signals exceed a predetermined threshold value. Hence, the transmit pulse sequence time interval always is restarted and runs to provide a new transmit signal after the occurrence of the last occurring interfering signal which is followed by the predetermined transmit sequence time interval.

This method is adaptive for the prevailing measuring conditions and, hence, the dead time of the measuring cycle is significantly reduced.

The present invention will be more clearly apparent from the following description when taken in conjunction with the accompanying drawings.

Figure 1:
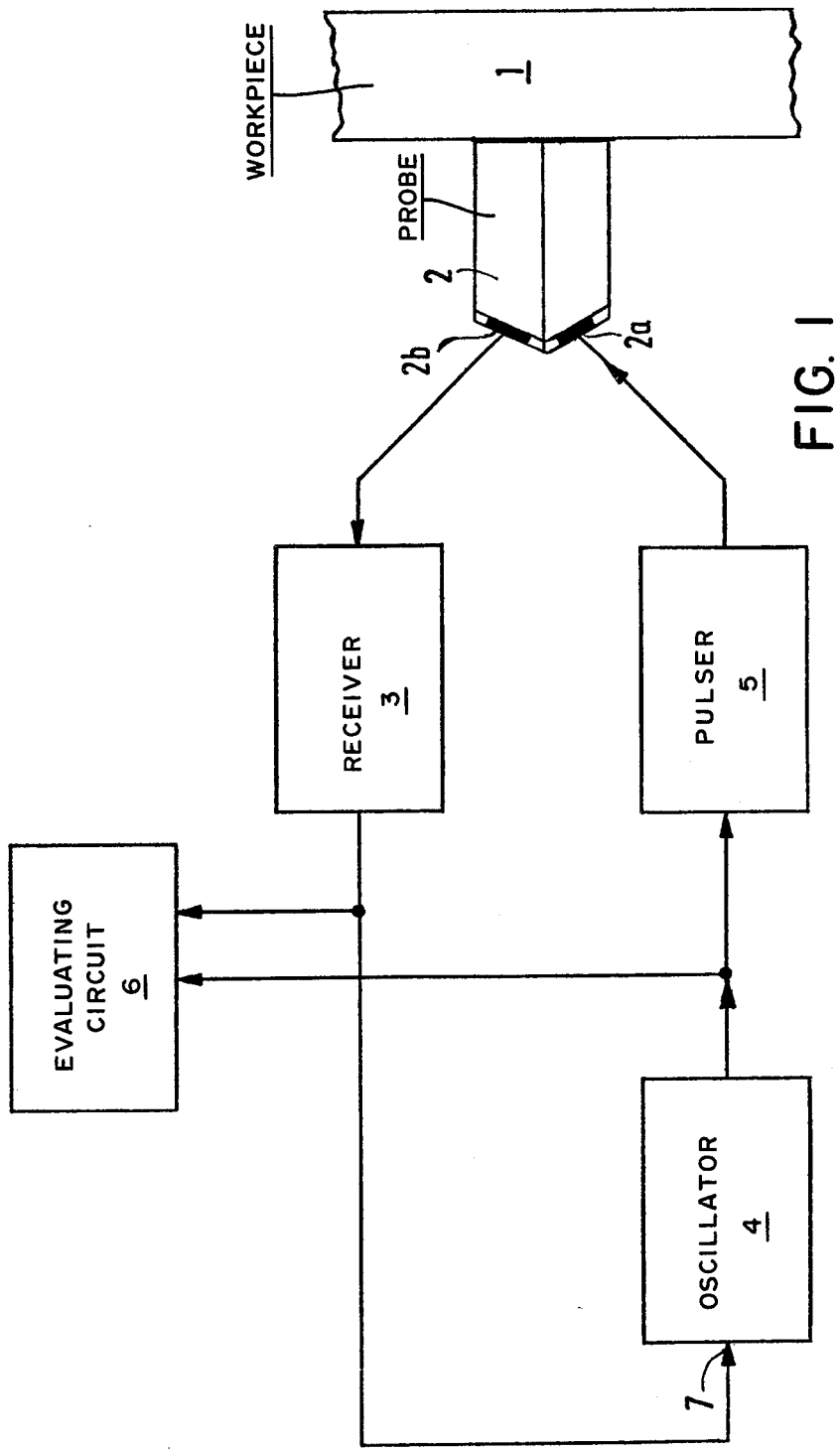
FIG. 1 is an electrical block diagram of a measuring system in accordance with the present invention.

DESCRIPTION OF THE INVENTION:

In accordance with the present method there is provided an oscillator 4, FIG. 1, which does not operate in the usual manner at a predetermined repetition frequency with constant time intervals between transmit pulses, but which operates at a frequency responsive to the echo signal sequence manifest at the receiver 3. Each echo responsive signal appearing at the output of the receiver 3, originating from the receive probe 2b of the transmit-receive probe 2 and resulting from an echo signal arising within the workpiece 1 or caused by cross-coupling of a transmit signal from the pulser 5 to the receiver 3, inhibits the oscillator 4 for a predetermined time interval $t_1$. Only after the passing of such time interval, does oscillator 4 provide a new pulse signal. If during the time interval $t_1$ a new echo signal is manifest at the input 7 of the oscillator 4, the oscillator 4 is reset and the time interval $t_1$ starts to run anew. Hence, the pulser 5 can provide a new transmit signal only after the passage of a time interval $t_1$ following the last received signal manifest at the input 7. In other words, a new transmit signal is generated only subsequent to the passing of time interval $t_1$ caused by the most recent signal capable of causing interference. Therefore, it is no longer necessary to provide for a long predetermined time interval (dead time) between successive transmit signals, but a new transmit pulse is generated after the passage of a time interval $t_1$ following the last received signal capable of causing interference. The time interval $t_1$ is selected to be slightly longer than the sum of the transit times within the test probe 2 and the time between successive multiple echo signals.

Block 6 of FIG. 1 designates the circuit for evaluating the signals and providing an indication of the workpiece thickness measured.

Figure 2:
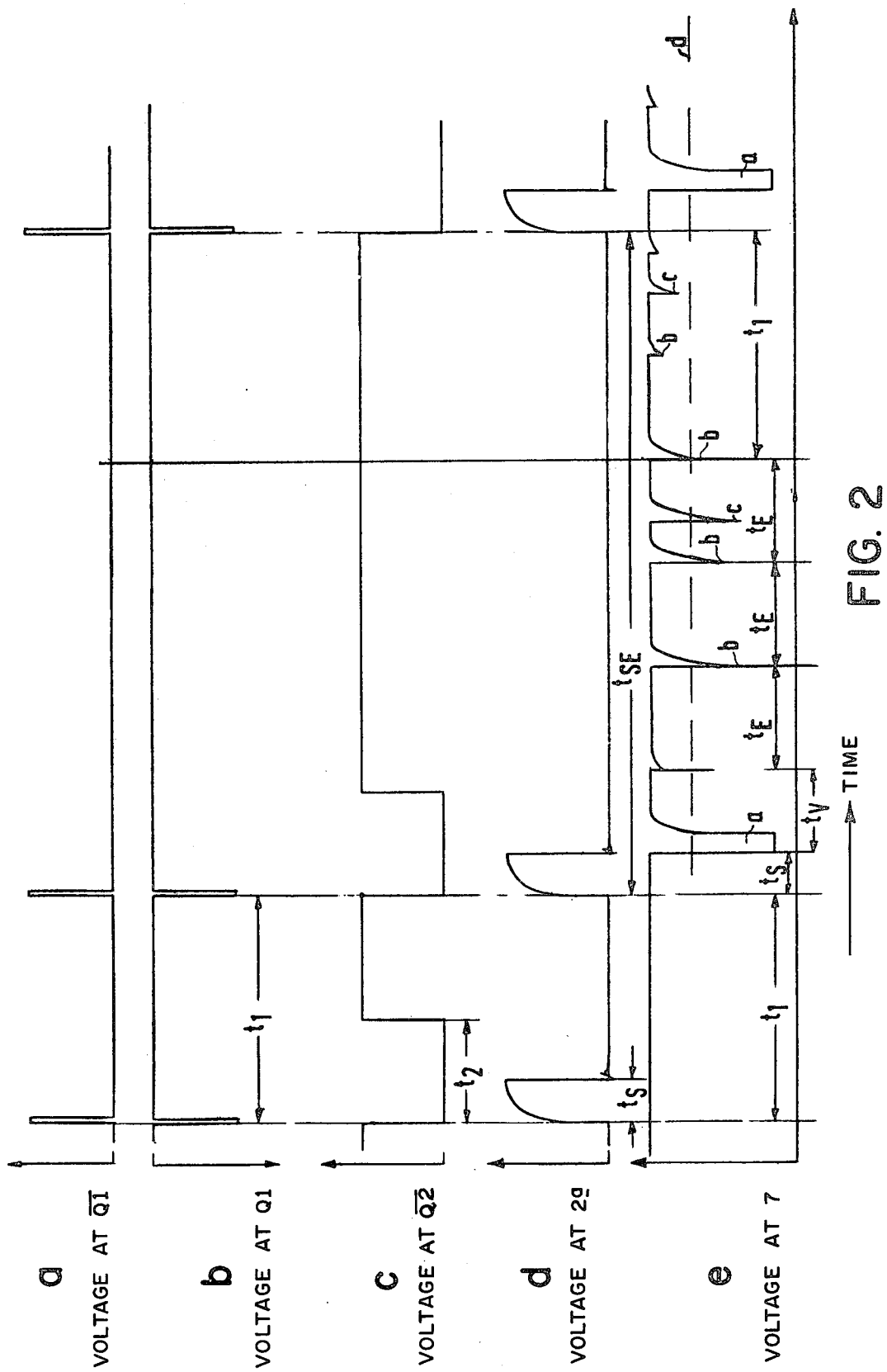
FIG. 2 is a timing diagram pertaining to the embodiment per FIG. 1.
Figure 3:
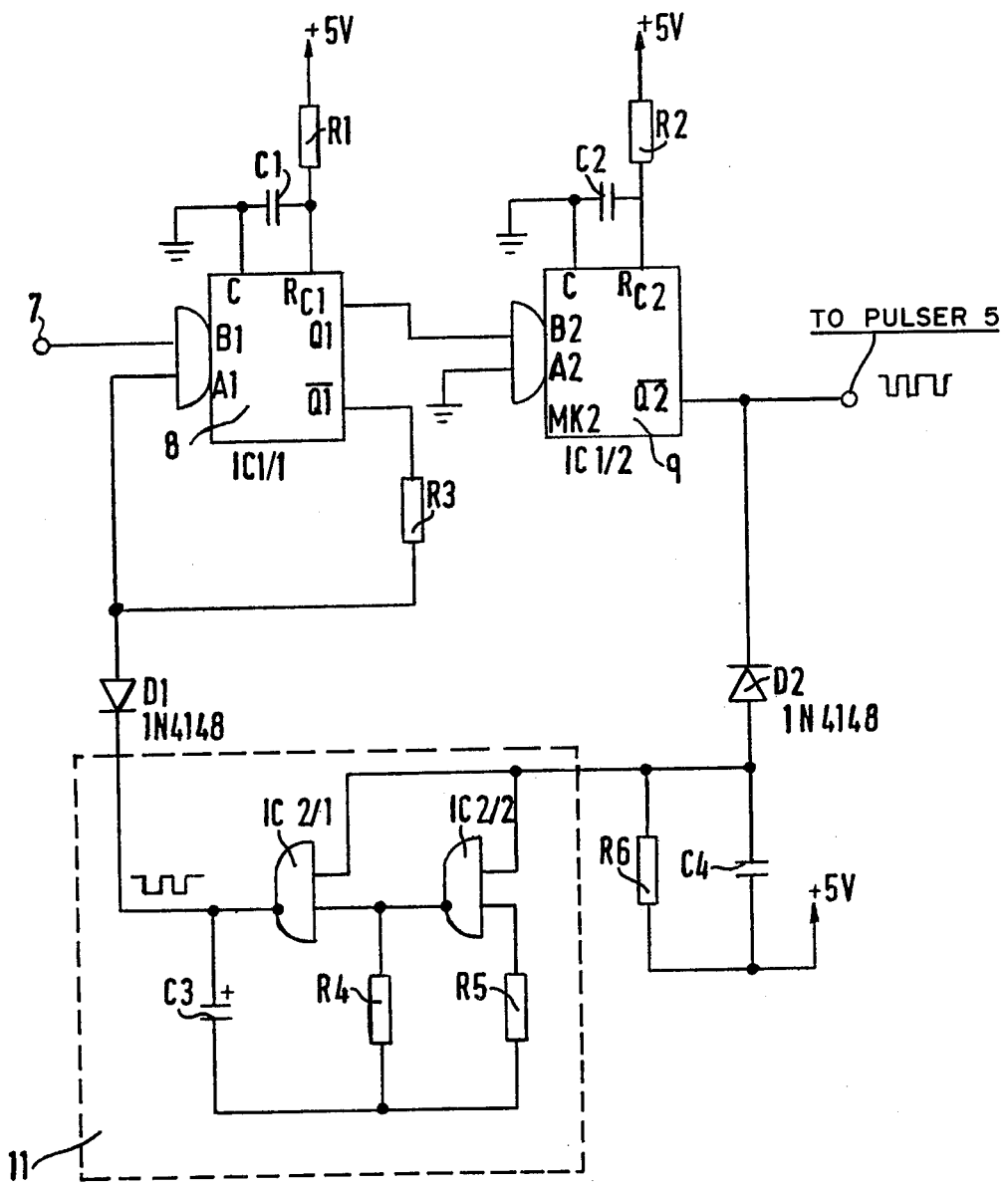
FIG. 3 is a schematic electrical circuit diagram of the oscillator used in FIG. 1.

Operation of the oscillator 4 will be described with reference to FIG. 3 and the associated timing diagram per FIG. 2. Commercially available integrated circuits IC1, for instance Motorola MC 14528 CP, and IC2, for instance Motorola MC 14011 CP, are used. When a positive voltage is applied at the input side 7 of the monostable multivibrator 8 (left portion of FIG. 2e), the multivibrator is triggered by itself from output terminal Q1 via resistor R3 to input terminal A1 to automatically retrigger the multivibrator 8. The multivibrator 8 remains in this triggered conditioned for a time interval $t_1$ depending upon the time constant determined by the values of resistor R1 and capacitor C1 (FIG. 3). As long as there is only a positive voltage applied at input 7 there is produced at terminals Q1 and Q1 a sequence of spike-shaped pulses occurring at a fixed time interval $t_1$ (FIG. 2b) which pulses are applied to the input terminal B2 of the monostable multivibrator 9. The multivibrator 9 is triggered responsive to each such pulse for a constant time interval $t_2$ which interval is determined by the time constant of resistor R2 and capacitor C2; however with the provision that the value of $t_2$ is less than the value of $t_1$. At the terminal Q2 of the multivibrator 9 there is a signal (FIG. 2c) which with its descending edge triggers the transmit pulse signal of the pulse generator 5, the transmit pulse signal having a duration of $t_S$. The steeply falling edge of the transmit pulse signal $t_S$ can cause by virtue of its high frequency portion interference at the input of the receiver 3, which interference then provides at the output of the receiver 3 of a pulse signal "a" shown in FIG. 2e. The signal "a" and the ensuing echo signals "b" and "c" which exceed the threshold value "d" always reset the monostable multivibrator, that is the predetermined time interval $t_1$ each time runs anew (retriggered stage 8). The following pulse signal at output Q2 occurs first at the time $t_1$ subsequent to the last evaluated echo signal "b" or "c". Curves "b" indicate the multiple echo signals arising from reflection at the workpiece rear surface, and curves "c" indicate the signals possible responsive to wave mode transformation, for instance shear waves.

Thus, if at the input 7 echo signals of sufficient amplitude are received, the multivibrator 8 is triggered resulting from the signal at terminal B1. The next succeeding transmit pulse resulting from the spike shaped trigger pulse at Q1 occurs only after the passage of time represented by the sequence of the signals received and to be evaluated and the constant trigger time interval $t_1$. As is evident from FIG. 2, the interval between two transmit signals $t_{SE}$ comprises:

$$t_{SE} = t_S + t_v + Zt_E + t_1$$

wherein $t_S$ = duration of transmit signal;
$t_V$ = total transit time of signal in the transducer probe from the active transmit crystal surface to the workpiece entrant surface and from the workpiece exit surface to the passive receive transducer crystal surface.

If for any reason triggering of stage 8 does not occur, for instance upon starting, an auxiliary oscillator 11 comprising capacitor C3, resistances R4, R5 and two IC2 circuits fulfills such function via diode D1. As soon as the primary oscillator operates or operates once again, i.e., the circuit comprising blocks 8 and 9, discernible by a potential change at terminal Q2, the auxiliary oscillator is rendered inoperative via diode D2, resistor R6 and capacitor C4.

A typical example taken from practice (100 mm thick aluminum workpiece) shall serve to illustrate the advantage derived from the present invention:

Measuring range $d_{max}$ = 100 mm for workpieces with acoustic velocities for longitudinal waves from 1,000 m/sec to 10,000 m/sec. Hence, $V_{Lmin}$ = 1,000 m/sec;

Maximum transit time in the transducer probe delay portions for a typical embodiment $t_{Vmax}$ = 10 $\mu$sec;

Maximum transmit pulse duration for the present embodiment $t_{Smax}$ = 10 $\mu$sec.

The duration $t_1$ at minimum must be the sum of twice the transit time for maximum workpiece thickness (measured distance $d_{max}$) and lowest occurring acoustic velocity increased by the transit time in the probe portions.

Hence, $$t_1 = \frac{2d_{max}}{V_{Lmin}} + t_V = \frac{2 \times 0.1m}{1,000 \text{ m/sec}} + 10 \text{ } \mu\text{sec} = 210 \text{ } \mu\text{sec}$$

The value $t_1$ is selected to be 211 $\mu$sec.

It is assumed furthermore that there are twenty rear surface echo signals above the threshold level and that echo signals due to wave mode conversion have died down earlier. Therefore:

$$t_{SE} = t_S + t_V + Zt_E + t_1$$

and $$t_{EAl} = \frac{2 \times 0.1m}{6300 \text{ m/sec}} \approx 32 \text{ } \mu\text{sec}$$

$t_{SEAl}$ = 10 $\mu$sec + 10 $\mu$sec + 20 × 32 $\mu$sec + 211 $\mu$sec = 871 $\mu$sec The entire measuring cycle $t_{ZAl} = n_{Al} \times t_{SEAl} = 630 \times 871$ $\mu$sec, hence, less than 0.55 sec contrasted with 2.5 sec in accordance with the present state of the art whereby Z = 20 applies as an assumption for the most unfavorable case. The factor Z will be smaller in the event there occur fewer rear wall responsive echo signals during a single or all of the measurements. Also, the measuring cycle becomes shorter when testing thin wall thicknesses as compared with the maximum wall thickness assumed in the above stated example. When the value of $t_E$ decreases the result will be a shortening of the dead time. The factor $Zt_E$, therefore, is variable and assumes a different value depending upon the particular measuring or test procedure.

While there has been described and illustrated a preferred embodiment of the present invention, it will be apparent to those skilled in the art that certain changes and modifications may be made without deviating from the principle and intent of this invention which shall be limited only by the scope of the appended claims.

What is claimed is:

1. The method of testing a workpiece by the ultrasonic pulse-echo technique comprising:
   periodically generating an electrical transmit pulse signal;
   applying said transmit pulse signal to an electroacoustic probe which is acoustically coupled to the surface of a workpiece for causing said probe to transmit in response to the receipt of a respective transmit pulse signal an ultrasonic search signal into the workpiece and to subsequently receive echo responsive acoustic signals arising from said search beam intercepting an acoustic discontinuity in the workpiece, and said probe producing corresponding echo responsive electrical signals, and
   inhibiting generating an electrical transmit pulse signal for a predetermined time interval responsive to the receipt at said probe of an echo responsive electrical signal exceeding a predetermined threshold amplitude value.

2. The method of testing a workpiece as set forth in claim 1, said predetermined time interval being selected to be greater than the sum of the acoustic signal transit times within the probe and the time between successive multiple echo signals caused in the workpiece and manifest at said probe.

3. A pulse-echo ultrasonic test circuit comprising:
   pulse generating means adapted to periodically generate an electrical transmit pulse signal;
   electroacoustic probe means coupled to said pulse generating means and a workpiece for receiving such transmit pulse signal and in response thereto transmit an ultrasonic search signal into the workpiece and receive ultrasonic echo signals arising from said search signal intercepting an acoustic discontinuity in the workpiece and for providing echo responsive electrical signals;
   receiving means coupled to said probe means for receiving said echo responsive electrical signals,
   control means coupled to said receiving means and to said pulse generating means for inhibiting said pulse generating means supplying a transmit pulse signal to said probe means for a predetermined period of time subsequent to receipt of an echo responsive electrical signal exceeding a predetermined threshold amplitude.

4. A pulse-echo ultrasonic test circuit as set forth in claim 3, said control means including a monostable multivibrator and said predetermined period of time being responsive to the time constant value of circuit components associated with said multivibrator.

5. A pulse-echo ultrasonic test circuit as set forth in claim 4, said monostable multivibrator being adapted to be triggered by itself and to be retriggered responsive to said echo responsive electrical signal exceeding a predetermined threshold amplitude.

* * * * *

UNITED STATES PATENT AND TRADEMARK OFFICE
CERTIFICATE OF CORRECTION

PATENT NO. : 4,098,131
DATED : July 4, 1978
INVENTOR(S) : Peter Renzel

It is certified that error appears in the above-identified patent and that said Letters Patent are hereby corrected as shown below:

Column 2, line 39, change "th" to read --the--.
Column 3, line 44, after "taking" insert --into account the--.
Column 4, line 47, change "Q1" to read --$\overline{Q1}$--;
        line 53, change second occurrence of "Q1" to read --$\overline{Q1}$--;
        line 61, change "Q2" to read --$\overline{Q2}$--;
        line 68, cancel second occurrence of the word "of".
Column 5, line 6, change "Q2" to read --$\overline{Q2}$--;
        line 22 (equation), change "$t_l$" to read --$t_1$--;
        line 37, change "Q2" to read --$\overline{Q2}$--;
        line 51, change "$t_l$" to read --$t_1$--;
        line 67 (equation) change "$t_l$" to read --$t_1$--.
Column 6, line 3 (equation), change "$t_{EA1}$" to read --$t_{EAl}$--;
        line 6 (equation), change "$t_{SEAL}$" to read --$t_{SEAl}$--;
        line 40, change "beam" to read --signal--.

Signed and Sealed this

Second Day of January 1979

[SEAL]

Attest:

RUTH C. MASON
Attesting Officer

DONALD W. BANNER
Commissioner of Patents and Trademarks